United States Patent
Shibata et al.

(10) Patent No.: US 7,094,934 B2
(45) Date of Patent: Aug. 22, 2006

(54) PRODUCTION PROCESS OF HYDROFLUOROCARBONS

(75) Inventors: Noriaki Shibata, Settsu (JP); Tatsuo Nakada, Settsu (JP); Takashi Shibanuma, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 706 days.

(21) Appl. No.: 10/182,820

(22) PCT Filed: Jan. 31, 2001

(86) PCT No.: PCT/JP01/00622

§ 371 (c)(1),
(2), (4) Date: Aug. 2, 2002

(87) PCT Pub. No.: WO01/56961

PCT Pub. Date: Aug. 9, 2001

(65) Prior Publication Data

US 2003/0060669 A1 Mar. 27, 2003

(30) Foreign Application Priority Data

Feb. 2, 2000 (JP) ............................... 2000-25259
Nov. 9, 2000 (JP) ............................... 2000-341797

(51) Int. Cl.
*C07C 17/087* (2006.01)
(52) U.S. Cl. ...................... 570/164; 570/101; 570/123; 570/161; 570/163; 570/165; 570/166; 570/167; 570/168; 570/170; 570/172; 570/191
(58) Field of Classification Search ................ 570/101, 570/123, 161, 163, 164–168, 170, 172, 191
See application file for complete search history.

(56) References Cited

FOREIGN PATENT DOCUMENTS

| | | |
|---|---|---|
| CN | 1168660 A | 12/1997 |
| DE | 0 729 932 A1 * | 1/1996 |
| EP | 0 767 158 A1 | 4/1997 |
| EP | 0 823 412 A1 | 2/1998 |
| JP | 7-233102 | 9/1995 |
| JP | 8-501551 | 2/1996 |
| JP | 8-217704 | 8/1996 |
| JP | 10-120602 | 5/1998 |
| WO | WO 94/06554 | 3/1994 |
| WO | WO 96/01797 | 1/1996 |
| WO | WO 99/26720 | 6/1999 |

OTHER PUBLICATIONS

M. Stacey et al., Advances in Fluorine Chemistry, vol. 3 (1963) pp. 188-217.
Chemical Engineering, vol. 106, No. 7, Jul. 1999, p. 21.

* cited by examiner

*Primary Examiner*—Samuel Barts
*Assistant Examiner*—Lansana Nyalley
(74) *Attorney, Agent, or Firm*—Birch, Stewart, Kolasch & Birch, LLP

(57) ABSTRACT

In a process for producing a hydrogen-containing fluorinated hydrocarbon in which a halogenated hydrocarbon reaction raw material, which includes a chlorinated alkene and/or a hydrogen-containing chlorinated alkane, is subjected to a fluorination reaction with hydrogen fluoride in a liquid phase in a reactor in the presence of a fluorination catalyst to obtain a reaction mixture which includes the hydrogen-containing fluorinated hydrocarbon, the reactor to be used has a portion which is able to contact with the reaction mixture, at least a part of this portion being made of an alloy material of 18 to 20% by weight of chromium, 18 to 20% by weight of molybdenum, 1.5 to 2.2% by weight of at least one element selected from niobium and tantalum and the balance of nickel.

23 Claims, No Drawings

US 7,094,934 B2

PRODUCTION PROCESS OF HYDROFLUOROCARBONS

This application is the national phase under 35 U.S.C. 371 of PCT International Application No. PCT/JP01/00622 which has an International filing date of Jan. 31, 2001, which designated the United States of America.

TECHNICAL FIELD

The present invention relates to a process for producing a hydrogen-containing fluorinated hydrocarbon and an apparatus therefor. It is to be noted that throughout the present specification, the term "hydrogen-containing fluorinated hydrocarbon" means a compound of hydrocarbon of which a part of hydrogen atoms is substituted by a fluorine atom(s) and which contains at least one hydrogen atom. The hydrogen-containing fluorinated hydrocarbon may or may not contain a chlorine atom(s). In terms of example, the hydrogen-containing fluorinated hydrocarbon includes a hydrogen-containing fluorinated alkane, a hydrogen-containing fluorinated alkene and the like. Additionally, the "part" of atoms may be one.

BACKGROUND ART

A chlorofluorocarbon generally known as a flon gas has been used for a foaming agent, a cleaning agent, and a refrigerant owing to its stable and thermal properties. The chlorofluorocarbon is a simple alkane such as methane or ethane of which all of hydrogen atoms are substituted by a chlorine atom(s) and/or a fluorine atom(s). Recently, such a chlorofluorocarbon has been subjected to regulation since the chlorofluorocarbon has been found to have a property of damaging the ozone layer.

Thus, demand of a hydrogen-containing fluorinated hydrocarbon which scarcely affects or does not affect the ozone layer has been increased and the development of such hydrogen-containing fluorinated hydrocarbon has been undertaken. The hydrogen-containing fluorinated hydrocarbon includes a hydrogen-containing fluorinated alkane, for example, 2,2-dichloro-1,1,1-trifluoroethane (also called as HCFC-123) and 1,1,1,3,3-pentafluoropropane (also called as HFC-245fa). HCFC-123 is a useful compound as a refrigerant for a turbo refrigerator or as an intermediate raw material for the production of 2-chloro-1,1,1,2-tetrafluoroethane (also called as HCFC-124) and pentafluoroethane (also called as HCFC-125). Further, HFC-245fa is a useful compound, for example, as a foaming agent which is not likely to damage the ozone layer.

In order to produce such a hydrogen-containing fluorinated hydrocarbon, the conventional process for producing a chlorofluorocarbon containing no hydrogen atom such as trichlorofluoromethane (also called as CFC-11), dichlorodifluoromethane (also called as CFC-12), and 1,1,2-trichlorotrifluoroethane (also called as CFC-113) can be applicable. As the conventional process for producing the chlorofluorocarbon, a process by reacting a chlorinated alkene and/or a chlorinated alkane with hydrogen fluoride in the presence of a fluorination catalyst to produce chlorofluorocarbon is known.

DISCLOSURE OF THE INVENTION

In the foregoing process for producing the chlorofluorocarbon, a reaction mixture has a corrosive property owing to the interaction of the fluorination catalyst and hydrogen fluoride. In the case of applying such a process to the production of the hydrogen-containing fluorinated hydrocarbon while adjusting reaction conditions, the reaction mixture shows an extremely intense corrosive property. Consequently, if a conventional and commonly used apparatus material, e.g. a stainless steel based material, is used for a reactor for the production of the hydrogen-containing fluorinated hydrocarbon in which a fluorination reaction is to be carried out, the reactor will be severely corroded and worn-out. Therefore, there occur problems of a shorter lifetime of the reactor and an increased facility cost.

For the material of the fluorination reactor, known nickel based materials such as Hastelloy B (trade name, having a representative compound of 62Ni-28Mo), Hastelloy C (trade name, having a representative compound of 54Ni-16Mo-16Cr), Inconel (trade name, having a representative compound of 76Ni-16Cr-7Fe), Monel (trade name, having a representative compound of 67Ni-33Cu) and so on are conventionally used at present (hereinafter such materials are also referred to as "conventional materials"). Such materials are recommended in, for example, WO 96/01797. However, the present inventors have tried producing the hydrogen-containing fluorinated hydrocarbon while using the reactor made of such a corrosion resistant alloy and have confirmed that the reactor is severely corroded in a portion which contacts with the reaction mixture in a liquid phase even though such material presents a high corrosion resistance compared with a stainless steel based material, so that the use of the reactor made of any one of these conventional materials during a long period is substantially impossible.

Such corrosion of the reactor may cause the release of a corrosion product into the reaction mixture and therefore may cause the contamination of the production process and the resultant product. This corrosion product (contaminant) decreases the reaction rate of the fluorination reaction and may be concerned in an unintended reaction to invite, for example, the inhibition of catalytic activity.

Then, it is suggested that the following reactors are employed for the fluorination reaction while considering the high corrosive property of the reaction mixture:

(1) A reactor made of a composite material which contains at least one corrosion resistant metal selected from the group consisting of gold, platinum, palladium, molybdenum, rhenium, and tungsten (see Japanese Patent Kohyo Publication No. 8-501551);

(2) A reactor made of fluororesin or a reactor lined with fluororesin (see Japanese Patent Kokai Publication No. 7-233102);

(3) A reactor having an inner surface made of a corrosion resistant metal material which contains aluminum (see Japanese Patent Kokai Publication No. 10-120602); and (4) A reactor which is installed in the inside of a container made of a metal material and at least of which inner surface is coated with fluororesin (see WO 99/26720).

However, all of the above described reactors (1) to (4) have defects and they are not necessarily optimum for the reactor to be employed for producing the hydrogen-containing fluorinated hydrocarbon. More specifically, in the case of (1), gold, platinum, palladium and rhenium among the corrosion resistant metals to be used for the reactor are not suitable to be used as a material for a large reactor in the industrial scale due to its expensiveness. As to molybdenum and tungsten, they have a disadvantage in that their mechanical strength can not be maintained sufficiently high since welded parts of such metals are very brittle on account of welding heat and a trace amount of a contaminant(s) which is introduced into the parts on welding. In addition, molybdenum and tungsten are inherently hard and brittle metal materials, and thus have much less workability. Therefore, it is substantially impossible to form an industrial scale reactor while employing these materials. In the case of using a resin material as in the reactors of (2) and (4), since the resin materials generally have a low thermal conductivity compared with metal materials, the resin materials make it very difficult to sufficiently transfer a necessary quantity of heat for gasifying a reaction product from the outside of the reactor, and especially in the case of using a reactor having a large capacity, it is difficult to control a reaction temperature. In the case of the reactor of (3), though the reactor has high corrosion resistance in a water-free condition, corrosion of the reactor extremely proceeds even when only a little amount of water is present in the reactor. Thus, maintenance of the reactor is extremely difficult. For example, water-washing can not be employed for periodic maintenance.

Hence, it is an object of the present invention to provide a new and more economical process for producing a hydrogen-containing fluorinated hydrocarbon in which hydrogen fluoride and at least one halogenated hydrocarbon as reaction raw materials (which are hereinafter also referred to as a "hydrogen fluoride reaction raw material" and a "halogenated hydrocarbon reaction raw material" respectively) are reacted with each other in the presence of the fluorination catalyst to obtain a reaction mixture comprising the hydrogen-containing fluorinated hydrocarbon as a reaction product, whereby at least one of the foregoing technological problems is alleviated, as well as to provide a reaction apparatus which is used for such a process.

The present invention provides a process for producing a hydrogen-containing fluorinated hydrocarbon in which at least one halogenated hydrocarbon reaction raw material selected from the group consisting of a chlorinated alkene and a hydrogen-containing chlorinated alkane is subjected to a fluorination reaction with a hydrogen fluoride reaction raw material in a liquid phase in a reactor in the presence of a fluorination catalyst so as to obtain a reaction mixture comprising the hydrogen-containing fluorinated hydrocarbon as a reaction product, which process comprises using the reactor having a reactor portion which is able to contact with the reaction mixture, at least a part of the reactor portion being made of an alloy material of 18 to 20% by weight of chromium, 18 to 20% by weight of molybdenum, 1.5 to 2.2% by weight of at least one element selected from niobium and tantalum and the balance of nickel. The term "% by weight" corresponds to "% by mass".

It is noted that the phrase "at least one element selected from niobium and tantalum" means either or both of niobium and tantalum. In the case of one of them is present alone, the value of "1.5 to 2.2% by weight" means the content of the one element. In the case of both of them are present, such value means the total content of them.

Said alloy material may include an element which is unavoidably immixed into it. The alloy material may further include not more than 1% by weight of cobalt, and may further include not more than 1% by weight of iron.

The phrase "reaction mixture" in the present invention means the liquid phase which exists in the reactor and contains the hydrogen-containing fluorinated hydrocarbon as the reaction product, more specifically contains the reaction raw materials and the fluorination catalyst in addition to the reaction product and may optionally contain a reaction solvent, which is mentioned after, and so on. The reaction mixture may contain the reaction raw materials and the reaction product in a gas phase while being dispersed in the liquid phase.

The phrase "reactor portion which is able to contact with the reaction mixture" in the present invention means a part of the reactor which part constantly contacts with the reaction mixture during the fluorination reaction. However, when there is a part in the reactor which part does not constantly contact but at least temporally contacts with the reaction mixture during the fluorination reaction depending on conditions of the fluorination reaction or owing to change in volume (or change in liquid level) of the reaction mixture which may be caused by change in quantity of the reaction raw materials to be processed, such part can be comprised in the phrase "reactor portion which is able to contact with the reaction mixture". Further, when there is a part which potentially contacts with the reaction mixture by splashing during the reaction, such part can be comprised in the phrase "reactor portion which is able to contact with the reaction mixture".

As to the reactor to be used according to the present invention, at least a part of, and preferably the whole of, the reactor portion which is able to contact with the reaction mixture, for example the inner surface of a bottom and sides of the reactor, and preferably the whole of the inner surface of the reactor, is made of said alloy material. The use of such reactor makes it possible to alleviate deterioration of the apparatus due to corrosion and conduct the reaction continuously during a long period with a high yield while not lowering the catalyst activity since the alloy material has a high corrosion resistance. Furthermore, the use of such reactor can make maintenance in routine work readier since the reactor has a sufficiently high corrosion resistance even when an amount of water may introduced into a reaction system for producing the hydrogen-containing fluorinated hydrocarbon upon maintenance.

An example of the alloy material which can be used for the process of the present invention is MAT 21 (trade name). Nominal composition of MAT 21 consists of 19% by weight of chromium, 19% by weight of molybdenum, 1.8% by weight of tantalum, 1% by weight or less of cobalt, 1% by weight or less of iron, and the balance of nickel. The balance may include an element(s) which can be unavoidably immixed at a extremely small amount.

This alloy material can be used as such to construct the reactor with the alloy material. Alternatively, the alloy material can be used in the form of a composite material including the layer of the alloy material to form at least a portion of the inner surface of the reactor with the layer of the alloy material, which portion is able to contact with the liquid phase. It is noted that the "composite material" in the specification means a material including layers of at least two different materials, in other words, a material including a surfacing (or cladding) and a base material which is laid under the surfacing.

In the case of using the composite material for the reactor, the present invention can be conducted while using the alloy material layer for the surfacing of the reactor which is exposed to the fluorination reaction. On the other hand, the base material is not required to have a high corrosion resistance since it is not exposed to (or does not contact with) the reaction mixture. Thus, a steel lumber or other metal material such as a carbon steel, a stainless steel, a nickel based alloy and aluminum is generally used for the base material, but not limited to these material as long as a material satisfies various conditions of properties required for the reactor such as strength, weldability, heat conductivity and so on, except for the corrosion resistant.

Additionally, an appropriate intermediate material can be provided between the base material and the layer of the alloy material (i.e. the surfacing) in order to improve adhesion between the base material and the surfacing.

As a method for manufacturing the composite material, there is a method by complexing (or cladding) the base material of any appropriate material with the surfacing of the alloy material according to a manner of, for example, hot rolling, explosive welding or the like. By using the composite material thus obtained, the reactor can be constructed in a predetermined form.

The alloy material having a high corrosion resistance as described above can be used not only as a material for the reactor but also as a material for any other devices which may be exposed to the fluorination reaction such as a stirrer, a pipe, a valve, a tube. Further, the alloy material can be used as a material of any container for storing and/or carrying the reaction mixture while containing it. In the case of using the alloy material for the devices other than the reactor, the alloy material can be also used as such to construct them, or can be used in the form of a composite material to form at least a portion of the inner surface of the reactor with the layer of the alloy material, which portion is able to contact with the liquid phase.

The alloy material has been preferably processed (or treated) so as to cause a residual stress in its surface portion. The corrosion resistance of the alloy material can become higher by processing the surface portion of the alloy material as described above. More concretely, manners of sandblasting, shot peening, grinding with a grinding stone or the like, polishing, impacting with a jet chisel and so on, but not limited to these, can be used for processing to cause the residual stress in the surface portion of the metal (the alloy material).

Alternatively, it is preferable that the alloy material has been subjected to a heat treatment. The corrosion resistance of the alloy material can be also enhanced by subjecting the alloy material to such a heat treatment. More concretely, manners of heating in an electric furnace, heating with a gas burner and so on can be used for subjecting the metal (the alloy material) to the heat treatment, but other manners can also be used as long as it can heat the metal. The heat treatment can be conducted so as to heat the surface portion of the metal or to heat the whole of the metal (that is, the surface portion and the inner portion of the metal). Though conditions of the heat treatment may be varied depending on the composition of the metal to be used, such conditions may include a temperature of, for example, 400 to 800° C. and preferably 500 to 600° C. and a period of, for example, not less than one hour and preferably not less than three hours. However, the present invention is not limited to this, and the conditions such as the heating temperature and the heating period can be changed appropriately depending on the metal to be used.

It is noted that both of the processing for causing the residual stress in the surface portion of the metal and the heat treatment can be applied in combination.

The fluorination catalyst which is employed in the present invention is generally a halide compound of one or more elements selected from the group consisting of antimony, niobium and tantalum, and preferably the catalyst is a chloride, a fluoride, or a chloro-fluoride. The fluorination catalyst may be a mixture of two or more halides containing different elements and/or different halogens. The fluorination catalyst includes one or more compounds selected from the group consisting of a halide having the valence of five (such as an antimony pentahalide, a niobium pentahalide and a tantalum pentahalide) and a halide having the valence of three (such as an antimony trihalide, a niobium trihalide and a tantalum trihalide). For example, the fluorination catalyst having the valence of five is one or more compounds selected from the group consisting of $SbF_5$, $SbClF_4$, $SbCl_2F_3$, $SbCl_3F_2$, $SbCl_4F$, $SbCl_5$, $NbF_5$, $NbClF_4$, $NbCl_2F_3$, $NbCl_3F_2$, $NbCl_4F$, $TaF_5$, $TaClF_4$, $TaCl_2F_3$, $TaCl_3F_2$, $TaCl_4F$ and $TaCl_5$. On the other hand, the fluorination catalyst having the valence of three is, for example, one or more compounds selected from the group consisting of $SbF_3$, $SbCl_2F$, $SbCl_3$, $SbClF_2$, $NbClF_2$, $NbF_3$, $TaCl_3$, $TaF_3$ and $TaClF_2$.

In addition to the halide having the valence of five, the fluorination catalyst may further include one or more of: an antimony halide having a different valence (i.e. a valence except for five) such as an antimony halide having the valence of three such as $SbF_3$ described in the above; and a halide of an element such as titanium and tin. The halide having the valence of three and the halide of element of titanium, tin and the like have a catalytic action which is less than that of the halide having the valence of five. However, it has been demonstrated that the corrosion of the reactor can be retarded by adding these halides, especially $SbF_3$ or the like, to the halide having the valence of five as described above. The fluorination reaction can be conducted while these halides having the relatively mild catalytic action and the halide having the valence of five are used and coexist in the reaction system.

As a starting material, at least one halogenated hydrocarbon reaction raw material selected from the group consisting of a chlorinated alkene and a hydrogen-containing chlorinated alkane. Through the present specification, the term "chlorinated alkene" means an alkene compound at least one of which hydrogen atom is substituted with a chlorine atom, and which may or may not contain a hydrogen atom and may or may not contain a fluorine atom. The term "hydrogen-containing chlorinated alkane" means a saturated hydrocarbon compound a part of which hydrogen atoms is substituted with a chlorine atom, and which contains at least one hydrogen atom, and which may or may not contain a fluorine atom. The chlorinated alkene and the hydrogen-containing chlorinated alkane preferably have a carbon number of 1 to 6, and more preferably a carbon number of 1 to 4. In the present specification, it should be understood that the chlorinated alkene and the hydrogen-containing chlorinated alkane include a partly fluorinated derivative of these compounds. The term "partly fluorinated compound" means a compound a part (but not all) of which chlorine atoms is substituted with a fluorine atom.

Concretely, the chlorinated alkene preferably includes a chlorinated ethylene (more preferably tetrachloroethylene, trichloroethylene), a chlorinated propene, a chlorinated butene and partly fluorinated compounds of these alkenes. The hydrogen-containing chlorinated alkane preferably includes a hydrogen-containing chlorinated methane (more preferably dichloromethane), a hydrogen-containing chlorinated ethane, a hydrogen-containing chlorinated propane, and partly fluorinated compounds of these alkanes.

The chlorinated ethylene can be expressed by the following general formula (1):

$$C_2H_aF_bCl_c \qquad (1)$$

(wherein a, b, and c are integers satisfying: a+b+c=4; a≧0; b≧0; and c≧1).

The hydrogen-containing chlorinated methane can be expressed by the following general formula (2):

$$CH_dF_eCl_f \qquad (2)$$

(wherein d, e, and f are integers satisfying: d+e+f=4; d≧1; e≧0; and f≧1).

The hydrogen-containing chlorinated ethane can be expressed by the following general formula (3):

$$C_2H_gF_hCl_i \qquad (3)$$

(wherein g, h, and i are integers satisfying: g+h+i=6; g≧1; h≧0; and i≧1).

The hydrogen-containing chlorinated propane can be expressed by the following general formula (4):

$$C_3H_jF_kCl_l \qquad (4)$$

(wherein j, k, and l are integers satisfying: j+k+l=8; j≧1; k≧0; and l≧1).

The chlorinated propene can be expressed by the following general formula (5):

$$C_3H_mF_nCl_o \qquad (5)$$

(wherein m, n, and o are integers satisfying: m+n+o=6; m≧0; n≧0; and o≧1).

The chlorinated butadiene can be expressed by the following general formula (6):

$$C_4H_pF_qCl_r \qquad (6)$$

(wherein p, q, and r are integers satisfying: p+q+r=6; p≧0; q≧0; and r≧1).

The hydrogen-containing fluorinated hydrocarbon as an aimed product is a compound having at least one hydrogen atom obtained by substitution of a part or all of chlorine atoms of a halogenated hydrocarbon as a starting material with a fluorine atom(s), or optionally by adding a fluorine atom and a hydrogen atom to at least one double bond of the chlorinated alkene by an addition reaction to decrease the number of the double bond(s). Consequently, the aimed product produced through the fluorination reaction may vary depending on the halogenated hydrocarbon as the starting material. Combinations of the starting materials and the preferable aimed products are as follows.

In the case where the halogenated hydrocarbon reaction raw material as the starting material is the chlorinated ethylene expressed by the foregoing general formula (1), the hydrogen-containing fluorinated hydrocarbon which is preferable as the aimed product is a hydrogen-containing fluorinated ethane expressed by the following general formula (7):

$$C_2H_{a+1}F_{b+w+1}Cl_{c-w} \qquad (7)$$

(wherein a, b, c and w are integers satisfying: a+b+c=4; a≧0; b≧0; c≧1; and 0≦w≦c). Particularly, the preferable combinations of the starting material/the aimed product, that is, the halogenated hydrocarbon/the hydrogen-containing fluorinated hydrocarbon in this case include: tetrachloroethylene/2,2-dichloro-1,1,1-trifluoroethane; trichloroethylene/2-chloro-1,1,1-trifluoroethane; vinylidene chloride/1,1,1,-trifluoroethane; vinyl chloride/1,1-difluoroethane; 1,1,1-trichloroethane/1,1,1-trifluoroethane; and the like.

In the case where the halogenated hydrocarbon reaction raw material as the starting material is the hydrogen-containing chlorinated methane expressed by the foregoing general formula (2), the hydrogen-containing fluorinated hydrocarbon which is preferable as the aimed product is a hydrogen-containing fluorinated methane expressed by the following general formula (8):

$$CH_dF_{e+x}Cl_{f-x} \qquad (8)$$

(wherein d, e, f and x are integers satisfying: d+e+f=4; d≧1; e≧0; f≧1; and 1≦x≦f). Particularly, the preferable combinations of the halogenated hydrocarbon/the hydrogen-containing fluorinated hydrocarbon in this case include: dichloromethane/difluoromethane; and the like.

In the case where the halogenated hydrocarbon reaction raw material as the starting material is the hydrogen-containing chlorinated ethane expressed by the foregoing general formula (3), the hydrogen-containing fluorinated hydrocarbon preferable as the aimed product is a hydrogen-containing fluorinated ethane expressed by the following general formula (9):

$$C_2H_gF_{h+y}Cl_{i-y} \qquad (9)$$

(wherein g, h, i and y are integers satisfying: g+h+i=6 g≧1; h≧0; i≧1; and 1≦y≦i). Particularly, the preferable combinations of the halogenated hydrocarbon/the hydrogen-containing fluorinated hydrocarbon in this case include: 1,1,1,2-tetrachloroethane/1,1,1-trifluoro-2-chloroethane; and the like.

In the case where the halogenated hydrocarbon reaction raw material as the starting material is the hydrogen-containing chlorinated propane expressed by the foregoing general formula (4), the hydrogen-containing fluorinated hydrocarbon preferable as the aimed product is a hydrogen-containing fluorinated propane expressed by the following general formula (10):

$$C_3H_jF_{k+z}Cl_{l-z} \qquad (10)$$

(wherein j, k, l and z are integers satisfying: j+k+l=8; j≧1; k≧0; l≧1 and 1≦z≦l). Particularly, the preferable combinations of the halogenated hydrocarbon/the hydrogen-containing fluorinated hydrocarbon in this case include: one or more substituted propanes selected from 1,1,1,3,3-pentachloropropane and a partially fluorinated compound thereof/1,1,1,3,3-pentafluoropropane; and the like.

The partially fluorinated compound of 1,1,1,3,3-pentachloropropane means a compound formed by partially substituting a part of chlorine atoms of 1,1,1,3,3-pentachloropropane with a fluorine atom(s). Examples of such compound include 1,1,3,3-tetrachloro-1-fluoropropane, 1,3,3-trichloro-1,1-difluoropropane, 3,3-dichloro-1,1,1-trifluoropropane, 3-chloro-1,1,1,3-tetrafluoropropane and the like.

In the case where the halogenated hydrocarbon reaction raw material as the starting material is the chlorinated propene expressed by the foregoing general formula (5), the hydrogen-containing fluorinated hydrocarbon preferable as an aimed product is a hydrogen-containing fluorinated propane expressed by the following general formula (11):

$$C_3H_{m+1}F_{n+u+1}Cl_{o-u} \qquad (11)$$

(wherein m, n, o and u are integers satisfying: m+n+o=6; m≧0; n≧0; o≧1; and 0≦u≦o). Particularly, the preferable combinations of the halogenated hydrocarbon/the hydrogen-containing fluorinated hydrocarbon in this case include: one or more substituted propenes selected from 1,1,1,2,3,3-hexachloropropene and partially fluorinated compounds thereof/2,3-dichloro-1,1,1,3,3-pentafluoropropane; one or more substituted propenes selected from 1,3,3,3-tetrachloropropene and partially fluorinated compounds thereof (e.g. 1-chloro-3,3,3-trifluoropropene)/1,1,3,3-pentafluoropropane; and the like.

The partially fluorinated compounds of 1,1,1,2,3,3-hexachloropropene mean compounds produced by partially substituting a part of chlorine atoms with a fluorine atom(s). Examples of such compounds include 2,3,3-trichloro-1,1,1-trifluoropropene, 1,2,3,3-tetrachloro-1,1-difluoropropene, 1,1,2,3,3-pentachloro-1-fluoropropene and the like.

Further in the case where the halogenated hydrocarbon reaction raw material as the starting material is the chlorinated propene expressed by the foregoing general formula (5), the hydrogen-containing fluorinated hydrocarbon preferable as an aimed product is a hydrogen-containing fluorinated propene expressed by the following general formula (11'):

$$C_3H_{m'}F_{n+u}Cl_{o-u'} \quad (11')$$

(wherein m', n, o and u' are integers satisfying: m'+n+o=6; m'≧1; n≧0; o≧1; and 1≦u'≦o). Particularly, the preferable combinations of the halogenated hydrocarbon/the hydrogen-containing fluorinated hydrocarbon in this case include: 1,3,3,3-tetrachloropropene/(1-chloro-3,3,3-trifluoropropene and/or 1,3,3,3-tetrafluoropropene); 1-chloro-3,3,3-trifluoropropene/1,1,1,3-tetrafluoropropene; and the like.

In the case where the halogenated hydrocarbon reaction raw material as the starting material is the chlorinated butadiene expressed by the foregoing general formula (6), the hydrogen-containing fluorinated hydrocarbon preferable as the aimed product is a hydrogen-containing fluorinated butene expressed by the following general formula (12):

$$C_4H_{p+1}F_{q+v+1}Cl_{r-v} \quad (12)$$

(wherein p, q, r and v are integers satisfying: p+q+r=6; p≧0; q≧0; r≧1; and 0≦v≦r). Particularly, the preferable combinations of the halogenated hydrocarbon/the hydrogen-containing fluorinated hydrocarbon in this case include: 1,1,2,3,4,4-hexachlorobutadiene/2-chloro-1,1,1,4,4,4-hexafluorobutene; and the like.

The amounts of the halogenated hydrocarbon and hydrogen fluoride, which are the reaction raw materials, and the fluorination catalyst may be any proper amounts respectively. A molar ratio of hydrogen fluoride to the halogenated hydrocarbon both of which are supplied as the reaction raw materials is preferably a stoichiometric molar ratio or higher, in other words hydrogen fluoride is preferably present superfluously. In general, while considering the efficiency of the reactor and the loss of unreacted hydrogen fluoride upon the recovery thereof, it is preferable to set the molar ratio of hydrogen fluoride to the halogenated hydrocarbon upon supplying them within the range from 1 to 10 times by mole, and especially from 1 to 5 times by mole.

In addition, the amount of the fluorination catalyst, it is preferably such that the fluorination catalyst is present in the reactor, but not limited to, at the ratio of 0 to 1 mole (excluding zero) and preferably 0.1 to 5 moles and alternatively the ratio of 25 to 90 moles and preferably 30 to 80 moles with respect to 100 moles in total of hydrogen fluoride and the fluorination catalyst which are present in the reactor. By setting the concentration of the fluorination catalyst within such range, it is possible to remarkably retard the corrosion of the reactor and to use the reactor during a long period. It is noted that the concentration of the fluorination catalyst means the molar concentration of the fluorination catalyst with respect to the total of hydrogen fluoride and the fluorination catalyst.

The fluorination reaction is generally conducted in the presence of a reaction solvent in addition to the reaction raw materials and the fluorination catalyst. In order to produce the aimed product at a high selectivity, it is particularly preferable to make hydrogen fluoride as the reaction raw material superfluously present with respect to the halogenated hydrocarbon reaction raw material so as to utilize hydrogen fluoride not only as the reaction material but also as the solvent.

In the particular case of using an antimony pentahalide as the fluorination catalyst, the antimony pentahalide is preferably present in the reactor at the ratio of not larger than 3 moles (excluding zero) and preferably a ratio of 0 to 2 moles (excluding zero), and alternatively the ratio of not smaller than 30 moles and preferably 40 to 80 moles with respect to 100 moles in total of hydrogen fluoride and the fluorination catalyst which are present in the reactor. In this case, hydrogen fluoride functions as the reaction solvent for the fluorination reaction as described above. By limiting the concentration of the antimony pentahalide within such range, it is possible to remarkably retard the corrosion of the reactor and to obtain a reaction rate which is efficient for a practical process. It is noted that the concentration of the antimony pentahalide means the molar concentration of the antimony pentahalide with respect to the total of hydrogen fluoride and the antimony pentahalide, and corresponds to the concentration of the fluorination catalyst in the case of using the antimony pentahalide as the fluorination catalyst.

Though the reaction materials of hydrogen fluoride and the halogenated hydrocarbon can be supplied either in a liquid phase or in a gas phase, the fluorination reaction is preferably proceeds in a liquid phase. This fluorination reaction is generally carried out in a normal or pressurized pressure. The reaction pressure, that is, the pressure of the inside of the reactor is preferably 0 to 20 kgf/cm$^2$ (0 to 1.96 MPa) of a gauge pressure, and more preferably 5 to 15 kgf/cm$^2$ (0.49 to 1.47 MPa) of a gauge pressure. The reaction temperature, that is, the temperature of the reaction mixture is preferably 0 to 175° C., and more preferably 20 to 120° C. Those reaction pressure ranges and temperature ranges are only examples, and the present invention is not intended to be limited to the foregoing exemplified ranges.

The process according to the present invention can be conducted in any one of a continuous manner and a batch manner.

In other aspect of the present invention, there is provided a reaction apparatus which is preferably used for the process for producing the hydrogen-containing fluorinated hydrocarbon, including the reactor having a reactor portion which is able to contact with the liquid phase, wherein at least a part of the reactor portion is made of an alloy material of 18 to 20% by weight of chromium, 18 to 20% by weight of molybdenum, 1.5 to 2.2% by weight of at least one element selected from niobium and tantalum and the balance of nickel.

The reaction apparatus according to the present invention may further include, in addition to said reactor, a jacket type heat exchanger and a stirrer or a mixer if they are required.

The present invention includes for example various embodiments (Modes 1 to 23) as follows:

(Mode 1) A process for a producing hydrogen-containing fluorinated hydrocarbon in which at least one halogenated hydrocarbon reaction raw material which is selected from the group consisting of a chlorinated alkene and a hydrogen-containing chlorinated alkane is subjected to a fluorination reaction with a hydrogen fluoride reaction raw material in a liquid phase in a reactor in the presence of a fluorination catalyst so as to obtain a reaction mixture which comprises the hydrogen-containing fluorinated hydrocarbon as a reaction product, which process comprises using the reactor having a reactor portion which is able to contact with the reaction mixture, wherein at least a part of the reactor portion is made of an alloy material of 18 to 20% by weight of chromium, 18 to 20% by weight of molybdenum, 1.5 to 2.2% by weight of at least one element selected from niobium and tantalum and the balance of nickel, the reactor portion which is able to contact with the reaction mixture.

(Mode 2) The process according to Mode 1 which comprises using the reactor wherein substantially the whole of the reactor portion which is able to contact with the reaction mixture is made of said alloy material.

(Mode 3(a)) The process according to Mode 1 or 2, wherein said alloy material has been processed so as to cause a residual stress in its surface portion.

(Mode 3(b)) The process according to any one of Modes 1, 2 and 3(a), wherein said alloy material has been subjected to a heat treatment. (Mode 4) The process according to any one of Modes 1 to 3, wherein the alloy material further contains not more than 1% by weight of cobalt.

(Mode 5) The process according to any one of Modes 1 to 4, wherein the alloy material further contains not more than 1% by weight of iron.

(Mode 6) The process according to any one of Modes 1 to 5, wherein the fluorination catalyst comprises at least one compound selected from the group consisting of an antimony pentahalide, a niobium pentahalide and a tantalum pentahalide, and an antimony trihalide, a niobium trihalide and a tantalum trihalide.

(Mode 7) The process according to any one of Modes 1 to 6, wherein the fluorination reaction is conducted in the presence of a reaction solvent, and hydrogen fluoride functions not only as the reaction raw material but also as the solvent.

(Mode 8) The process according to Mode 6, wherein an antimony pentahalide is used as the fluorination catalyst and present in the reactor in a ratio of not larger than 3 moles or not smaller than 30 moles with respect to 100 moles in total of hydrogen fluoride and the antimony pentahalide which are present in the reactor.

(Mode 9) The process according to any one of Modes 1 to 8, wherein the halogenated hydrocarbon reaction raw material is a chlorinated ethylene which is expressed by the following general formula (1):

$$C_2H_aF_bCl_c \quad (1)$$

wherein a, b, and c are integers satisfying: $a+b+c=4$; $a \geq 0$; $b \geq 0$; and $c \geq 1$.

(Mode 10) The process according to any one of Modes 1 to 8, wherein the halogenated hydrocarbon reaction raw material is a hydrogen-containing chlorinated methane which is expressed by the following general formula (2):

$$CH_dF_eCl_f \quad (2)$$

wherein d, e, and f are integers satisfying: $d+e+f=4$; $d \geq 1$; $e \geq 0$; and $f \geq 1$.

(Mode 11) The process according to any one of Modes 1 to 8, wherein the halogenated hydrocarbon reaction raw material is a hydrogen-containing chlorinated ethane which is expressed by the following general formula (3):

$$C_2H_gF_hCl_i \quad (3)$$

wherein g, h, and i are integers satisfying: $g+h+i=6$; $g \geq 1$; $h \geq 0$; and $i \geq 1$.

(Mode 12) The process according to any one of Modes 1 to 8, wherein the halogenated hydrocarbon reaction raw material is a hydrogen-containing chlorinated propane which is expressed by the following general formula (4):

$$C_3H_jF_kCl_l \quad (4)$$

wherein j, k, and l are integers satisfying: $j+k+l=8$; $j \geq 1$; $k \geq 0$; and $l \geq 1$.

(Mode 13) The process according to any one of Modes 1 to 8, wherein the halogenated hydrocarbon reaction raw material is a chlorinated propene which is expressed by the following general formula (5):

$$C_3H_mF_nCl_o \quad (5)$$

wherein m, n, and o are integers satisfying: $m+n+o=6$; $m \geq 0$; $n \geq 0$; and $o \geq 1$.

(Mode 14) The process according to any one of Modes 1 to 8, wherein the halogenated hydrocarbon reaction raw material is a chlorinated butadiene which is expressed by the following general formula (6):

$$C_4H_pF_qCl_r \quad (6)$$

wherein p, q, and r are integers satisfying: $p+q+r=6$; $p \geq 0$; $q \geq 0$; and $r \geq 1$.

(Mode 15) The process according to Mode 9, wherein the halogenated hydrocarbon reaction raw material is tetrachloroethylene and the hydrogen-containing fluorinated hydrocarbon which is produced through the reaction is 2,2-dichloro-1,1,1-trifluoroethane.

(Mode 16) The process according to Modes 9, wherein the halogenated hydrocarbon reaction raw material is trichloroethylene and the hydrogen-containing fluorinated hydrocarbon which is produced through the reaction is 2-chloro-1,1,1-trifluoroethane.

(Mode 17) The process according to Mode 10, wherein the halogenated hydrocarbon reaction raw material is dichloromethane and the hydrogen-containing fluorinated hydrocarbon which is produced through the reaction is difluoromethane.

(Mode 18) The process according to Mode 12, wherein the halogenated hydrocarbon reaction raw material is at least one substituted propane selected from the group consisting of 1,1,1,3,3-pentachloropropane and a partially fluorinated compound thereof and the hydrogen-containing fluorinated hydrocarbon which is produced through the reaction is 1,1,1,3,3-pentafluoropropane.

(Mode 19) The process according to Mode 13, wherein the halogenated hydrocarbon reaction raw material is 1,3,3,3-tetrachloropropene and the hydrogen-containing fluorinated hydrocarbon which is produced through the reaction is 1,1,1,3,3-pentafluoropropane.

(Mode 20) The process according to Mode 13, wherein the halogenated hydrocarbon reaction raw material is 1-chloro-3,3,3-trifluoropropene and the hydrogen-containing fluorinated hydrocarbon which is produced through the reaction is 1,1,1,3,3-pentafluoropropane.

(Mode 21) The process according to Mode 13, wherein the halogenated hydrocarbon reaction raw material is at least one substituted propene selected from the group consisting of 1,1,1,2,3,3-hexachloropropene and a partially fluorinated compound thereof and the hydrogen-containing fluorinated hydrocarbon which is produced through the reaction is 2,3-dichloro-1,1,1,3,3-pentafluoropropane.

(Mode 22) The process according to Mode 14, wherein the halogenated hydrocarbon reaction raw material is 1,1,2,3,4,4-hexachlorobutadiene and the hydrogen-containing fluorinated hydrocarbon which is produced through the reaction is 2-chloro-1,1,1,4,4,4-hexafluorobutene.

(Mode 23) A reaction apparatus which is used in the process for producing a hydrogen-containing fluorinated hydrocarbon according to any one of Modes 1 to 22, comprising a reactor having a reactor portion which is able to contact with a liquid phase, at least a part of the reactor portion being made of an alloy material of 18 to 20% by weight of chromium, 18 to 20% by weight of molybdenum, 1.5 to 2.2% by weight of at least one element selected from niobium and tantalum and the balance of nickel.

BEST MODE FOR CARRYING OUT THE INVENTION

Hereinafter, one embodiment of the present invention will be described in detail. In this Embodiment, MAT 21 (trade name) is used as the alloy material of 18 to 20% by weight of chromium, 18 to 20% by weight of molybdenum, 1.5 to 2.2% by weight of at least one element selected from niobium and tantalum and the balance of nickel.

As a reactor in which the fluorination reaction is conducted, a reactor is used which is constructed with the composite material and has a inner surface portion made of only MAT 21. This reactor may be manufactured according to an appropriate manner of metalworking which is known to the skilled person in the art (see, for example, Japanese Kohyo publication H8-501551). For example, a composite material which is formed by explosive welding of MAT 21 on to one side of a sheet of a base material consisting of any appropriate material as described above is shaped into parts having a predetermined shape by rolling or the like, and these parts are put together by welding or the like so as to locate the surfacing (MAT 21) on the inner side of the reactor, whereby the reactor having the inner surface portion made of MAT 21 alone can be manufactured.

A jacket type heat exchanger is set on the external of the reaction apparatus described above for supplying an amount of heat to the reaction mixture so as to gasify a fraction containing the reaction product. Furthermore, a stirrer or a mixer is installed in the reactor to stir or mix the reaction mixture so as to improve the efficiency of the reaction.

Next, the process for producing a hydrogen-containing fluorinated hydrocarbon using the above described reaction apparatus will be described below. At first, a liquid state hydrogen fluoride (HF) reaction raw material and a halogenated hydrocarbon reaction raw material are supplied through, for example, an introduction conduit to the reactor which is previously provided with the fluorination catalyst. Though the hydrogen fluoride reaction raw material and the halogenated hydrocarbon reaction raw material may be supplied either in liquid phase or in a gas phase, the fluorination reaction preferably proceeds in a liquid phase.

Hydrogen fluoride and a halogenated hydrocarbon introduced as described above are subjected to the fluorination reaction in the reactor in the presence of the fluorination catalyst to produce a reaction mixture containing a hydrogen-containing fluorinated hydrocarbon as a reaction product. The reaction mixture containing at least the reaction product produced through this fluorination reaction is supplied with an amount of heat by means of, for example, the jacket type heat exchanger, so that a fraction containing the reaction product is gasified and taken out. Therefore, the hydrogen containing fluorinated hydrocarbon as the aimed reaction product can be obtained.

In this embodiment, the supply of the amount of heat is achieved by heat conduction of the amount of heat, which is emitted from the jacket type heat exchanger, to the reaction mixture through the reactor. Thus, the metal material which has a high heat conductivity as described above is preferably used for the reactor.

Alternatively, the fraction which contains the reaction product may be taken out from the reactor in the form of liquid, and the liquid can be subjected to an operation such as liquid separation so as to obtain the hydrogen-containing fluorinated hydrocarbon as the aimed product with a high purity from the liquid.

The fluorination reaction itself has been already known and its reaction conditions (such as the temperature, the pressure, and the supply amounts of the catalyst and the reaction raw materials) can easily be selected by those skilled in the art. For example, see "ADVANCES IN FLUORINE CHEMISTRY", vol. 3, (1963).

Though the reaction apparatus of the present invention is preferably used to carry out the process for producing the hydrogen-containing fluorinated hydrocarbon, the reaction apparatus is not limited to this purpose and can also be used for carrying out other reactions in which a reaction mixture has a extremely high corrosive property.

INDUSTRIAL APPLICABILITY

The present invention provides the process for producing the hydrogen-containing fluorinated hydrocarbon which uses the reactor having an extremely high corrosion resistance compared to that of the conventional material. The reactor has advantages of workability similar to that of the conventional material and of facility of maintenance in a routine work.

EXAMPLES

Example 1

In this example, an autoclave of which inner surface portion is made of MAT 21 alone and which has a capacity of 500 ml was used as the reactor. 30 g (0.1 mol) of $SbCl_5$ as a fluorination catalyst and 200 ml (10 mol) of liquid-state hydrogen fluoride were previously introduced into the reactor. This liquid-state hydrogen fluoride was a reaction raw material and also had a function as a reaction solvent for the reaction. At that time, the fluorination catalyst ($SbCl_5$ as an antimony pentahalide in this example) was present in the reactor at an amount of 1 mole with respect to 100 moles of hydrogen fluoride, and therefore at an amount of about 1 mole with respect to 100 moles in total of hydrogen fluoride and the fluorination catalyst (the antimony pentahalide).

While the temperature of the reaction mixture in the reactor, i.e. the reaction temperature, being controlled at 80° C. and the pressure in the reactor, i.e. the reaction pressure, being kept at 1.1 MPa (gauge pressure), the reactor was supplied through respective inlets with liquid-state 1,1,1,3,3-pentachloropropane as a halogenated hydrocarbon reaction raw material at a rate of 30 g/h as well as liquid-state hydrogen fluoride with controlling the amount of liquid-phase hydrogen fluoride so as to keep the weight of the reactor and its content constant (in other words, so as to keep a level of a liquid phase constant), whereby liquid-phase fluorination reaction was carried out. The supplied rate of liquid-state hydrogen fluoride was 16.7 g/h on an average.

In such a manner just described above, a fraction which contained a gaseous reaction product (which also contained unreacted HF and HCl byproduct) was obtained through an outlet located on the upper portion of the reactor. The fraction contained hydrogen-containing fluorinated hydrocarbons (equivalent to about 18 kg/h). The hydrogen-containing fluorinated hydrocarbons contained 99% by mole or higher of 1,1,1,3,3-pentafluoropropane as a main product and slight amounts (less than 1% by mole) of 3-chloro-1,1,1,3-tetrafluoropropane and 3,3-dichloro-1,1,1-trifluoropropane as byproducts.

After the operation for 120 hours under the above described conditions, the reaction was stopped. The inner surface of the reactor (the autoclave) was investigated as to the corrosion by eye observation and corrosion was not found at all. After the reaction was stopped, a sample of the reaction liquid was obtained and subjected to titrimetry and atomic absorption spectrophotometry. From results of these analyses, it was found that the fluorination catalyst was maintained at the concentration which is substantially the same as that at the beginning of the reaction.

Example 2

A reactor similar to that used in Example 1 was used. Conditions as to this example were similar to in Example 1 unless otherwise indicated, and this was also applicable to following Examples 3 to 5.

36 g (0.1 mol) of $TaCl_5$ as a fluorination catalyst and 200 ml (10 mol) of liquid-state hydrogen fluoride as in Example 1 were previously introduced. At that time, the fluorination catalyst ($TaCl_5$ in this example) was present in the reactor at an amount of 1 mole with respect to 100 moles of hydrogen fluoride, and therefore at an amount of about 1 mole with respect to 100 moles in total of hydrogen fluoride and the fluorination catalyst. Then, while the reaction temperature being controlled at 80° C. and the reaction pressure being kept at 1.1 MPa (gauge pressure) as in Example 1, the reactor was supplied with liquid-state 1,1,1,2,3,3-hexachloropropene as a halogenated hydrocarbon reaction raw material at a rate of 34.5 g/h as well as liquid-state hydrogen fluoride with controlling the amount of liquid-phase hydrogen fluoride so as to keep the weight of the reactor and its content constant (in other words, so as to keep a level of a liquid phase constant), whereby liquid-phase fluorination reaction was carried out. The supplied rate of liquid-state hydrogen fluoride was 39.2 g/h on an average.

In such a manner just described above, a fraction which contained hydrogen-containing fluorinated hydrocarbons (equivalent to about 27.5 g/h) was obtained. The hydrogen-containing fluorinated hydrocarbons of the fraction contained 99% by mole or higher of 2,3-dichloro-1,1,1,3,3-pentafluoropropane as a main product and a slight amount (less than 1% by mole) of 2,3,3-trichloro-1,1,1,3-tetrafluoropropane as a byproduct.

After the operation for 120 hours under the above described conditions, the reaction was stopped. The inner surface of the reactor (the autoclave) was investigated as to the corrosion by eye observation and corrosion was not found at all. After the reaction was stopped, a sample of the reaction liquid was obtained and subjected to titrimetry and atomic absorption spectrophotometry. From results of these analyses, it was found that the fluorination catalyst was maintained at the concentration which is substantially the same as that at the beginning of the reaction.

Example 3

As similarly to Example 1, 30 g (0.1 mol) of $SbCl_5$ as a fluorination catalyst and 200 ml (10 mol) of liquid-state hydrogen fluoride were previously introduced. At that time, as similarly to Example 1, the fluorination catalyst ($SbCl_5$ as an antimony pentahalide in this example) was present in the reactor at an amount of about 1 mole with respect to 100 moles in total of hydrogen fluoride and the fluorination catalyst (the antimony pentahalide). Then, while the reaction temperature being controlled at 80° C. and the reaction pressure being kept at 1.1 MPa (gauge pressure) as in Example 1, the reactor was supplied with liquid-state trichloroethylene as a halogenated hydrocarbon reaction raw material at a rate of 18.2 g/h as well as liquid-state hydrogen fluoride with controlling the amount of liquid-phase hydrogen fluoride so as to keep the weight of the reactor and its content constant (in other words, so as to keep a level of a liquid phase constant), whereby liquid-phase fluorination reaction was carried out. The supplied rate of liquid-state hydrogen fluoride was 11.1 g/h on an average.

In such a manner just described above, a fraction which contained hydrogen-containing fluorinated hydrocarbons (equivalent to about 15.9 g/h) was obtained. The hydrogen-containing fluorinated hydrocarbons of the fraction contained 99% by mole or higher of 2-chloro-1,1,1-trifluoroethane as a main product and a slight amount (less than 1% by mole) of 1,2-dichloro-1,1-difluoroethane as a byproduct.

After the operation for 120 hours under the above described conditions, the reaction was stopped. The inner surface of the reactor (the autoclave) was investigated as to the corrosion by eye observation and corrosion was not found at all. After the reaction was stopped, a sample of the reaction liquid was obtained and subjected to titrimetry and atomic absorption spectrophotometry. From results of these analyses, it was found that the fluorination catalyst was maintained at the concentration which is substantially the same as that at the beginning of the reaction.

Example 4

As similarly to Example 1, 30 g (0.1 mol) of $SbCl_5$ as a fluorination catalyst and 200 ml (10 mol) of liquid-state hydrogen fluoride were previously introduced. At that time, as similarly to Example 1, the fluorination catalyst ($SbCl_5$ as an antimony pentahalide in this example) was present in the reactor at an amount of about 1 mole with respect to 100 moles in total of hydrogen fluoride and the fluorination catalyst (the antimony pentahalide). Then, while the reaction temperature being controlled at 100° C. and the reaction pressure being kept at 1.5 MPa (gauge pressure), the reactor was supplied with liquid-state tetrachloroethylene as a halogenated hydrocarbon reaction raw material at a rate of 23.0 g/h as well as liquid-state hydrogen fluoride with controlling the amount of liquid-phase hydrogen fluoride so as to keep the weight of the reactor and its content constant (in other words, so as to keep a level of a liquid phase constant), whereby liquid-phase fluorination reaction was carried out. The supplied rate of liquid-state hydrogen fluoride was 14.8 g/h on an average.

In such a manner just described above, a fraction which contained hydrogen-containing fluorinated hydrocarbons (equivalent to about 19.8 g/h) was obtained. The hydrogen-containing fluorinated hydrocarbons of the fraction contained 99% by mole or higher of 2,2-dichloro-1,1,1-trifluoroethane as a main product and a slight amount (less than 1% by mole) of 2,3-dichloro-1,1-difluoroethane as a byproduct.

After the operation for 120 hours under the above described conditions, the reaction was stopped. The inner surface of the reactor (the autoclave) was investigated as to the corrosion by eye observation and corrosion was not found at all. After the reaction was stopped, a sample of the reaction liquid was obtained and subjected to titrimetry and atomic absorption spectrophotometry. From results of these analyses, it was found that the fluorination catalyst was maintained at the concentration which is substantially the same as that at the beginning of the reaction.

Example 5

As similarly to Example 1, 30 g (0.1 mol) of $SbCl_5$ as a fluorination catalyst and 200 ml (10 mol) of liquid-state hydrogen fluoride were previously introduced. At that time, as similarly to Example 1, the fluorination catalyst ($SbCl_5$ as an antimony pentahalide in this example) was present in the reactor at an amount of about 1 mole with respect to 100 moles in total of hydrogen fluoride and the fluorination catalyst (the antimony pentahalide). Then, while the reaction temperature being controlled at 100° C. and the reaction pressure being kept at 1.1 MPa (gauge pressure), the reactor was supplied with liquid-state 1,1,2,3,4,4-hexachlorobutadiene as a halogenated hydrocarbon reaction raw material at a rate of 36.2 g/h as well as liquid-state hydrogen fluoride with controlling the amount of liquid-phase hydrogen fluoride so as to keep the weight of the reactor and its content constant (in other words, so as to keep a level of a liquid phase constant), whereby liquid-phase fluorination reaction was carried out. The supplied rate of liquid-state hydrogen fluoride was 22.0 g/h on an average.

In such a manner just described above, a fraction which contained hydrogen-containing fluorinated hydrocarbons (equivalent to about 26.9 g/h) was obtained. The hydrogen-containing fluorinated hydrocarbons of the fraction contained 98% by mole or higher of 2-chloro-1,1,1,4,4,4-hexafluorobutene as a main product and slight amounts (less than 2% by mole) of butenes as byproducts which were less fluorinated.

After the operation for 120 hours under the above described conditions, the reaction was stopped. The inner surface of the reactor (the autoclave) was investigated as to the corrosion by eye observation and corrosion was not found at all. After the reaction was stopped, a sample of the reaction liquid was obtained and subjected to titrimetry and atomic absorption spectrophotometry. From results of these analyses, it was found that the fluorination catalyst was maintained at the concentration which is substantially the same as that at the beginning of the reaction.

(Comparative Test)

In this comparative test, immersion tests were conducted as to some nickel based alloys (MAT 21, Hastelloy B2, Hastelloy C22, Monel 400 and Inconel 600) by using test pieces made of these materials. These alloys were evaluated through this test whether they are suitable for the material of the reactor for producing a hydrogen-containing fluorinated hydrocarbon or not.

Chemical compositions of the used alloy materials were generally as follows:
MAT 21: Cr 19%, Mo 19%, Nb 0%, Ta 1.8%, Co≦1%, Fe≦1%, and the balance of Ni.
Hastelloy B2: Cr≦1%, Mo 26–30%, Fe≦2%, Mn≦1%, Co≦1%, and the balance of Ni.
Hastelloy C22: Cr 20–22.5%, Mo 12.5–14.5%, W 2.5–3.5%, Fe 2.0–6.0%, Co≦2.5%, and the balance of Ni.
Monel 400: Fe<2.5%, Cu 28–34% and not less than 63% of Ni.
Inconel 600: Cr 14–17%, Fe 6–10% and not less than 72% of Ni.

In the chemical compositions described above, an slight amounts of elements which are unavoidably immixed are omitted.

The evaluation was based on the corrosion rate of the test piece which is calculated by an equation as below:

$$\text{Corrosion Rate (mm/year)} = \frac{87.60 \times \text{Corrosoin Loss (mg)}}{\text{Density (g/cm}^3\text{)} \times \text{Test Piece Surface Area (cm}^2\text{)} \times \text{Immersion Period (hour)}}$$

In the equation, the corrosion loss is a value obtained by subtracting the weight of the test piece after the test from that before the test. In order to obtain this value, test pieces were weighed beforehand and subjected to tests 1 to 3 respectively which are hereinafter described in detail, and the resultant test pieces were lightly rubbed with a rubber sheet to remove corrosion products and subjected to ultrasonic cleanings by means of water and acetone and thereafter weighed.

(Test 1)

The test piece having a size of about 30 mm×10 mm×3 mm was attached to the inside of an autoclave (volume: 1 liter) such that the test piece is completely immersed in the reaction mixture during the fluorination reaction. The autoclave was made of Hastelloy C and lined with polytetrafluoroethylene resin (PTFE) on its inner surface. 60 g (0.2 mol) of $SbCl_5$ as a fluorination catalyst and 400 ml (20 mol) of liquid-state hydrogen fluoride were introduced into the autoclave. At that time, the fluorination catalyst ($SbCl_5$ as an antimony pentahalide in this test) was present in the reactor at an amount of 1 mole with respect to 100 moles of hydrogen fluoride, and therefore at an amount of about 1 mole with respect to 100 moles in total of hydrogen fluoride and the fluorination catalyst (the antimony pentahalide). Then, while the reaction temperature being controlled at 80° C. and the reaction pressure being kept at 1.1 MPa (gauge pressure), the reactor was supplied with liquid-state 1,1,1,3,3-pentachloropropane as a halogenated hydrocarbon reaction raw material at a rate of 60 g/h as well as liquid-state hydrogen fluoride with controlling the amount of liquid-phase hydrogen fluoride so as to keep the weight of the reactor and its content constant (in other words, so as to keep a level of a liquid phase constant), whereby liquid-phase fluorination reaction was carried out. The supplied rate of liquid-state hydrogen fluoride was 33.4 g/h on an average.

In such a manner just described above, a fraction which contained a gaseous reaction product (which also contained unreacted HF and HCl byproduct) was obtained. The fraction contained hydrogen-containing fluorinated hydrocarbons (equivalent to about 36 g/h). The hydrogen-containing fluorinated hydrocarbons contained 99% by mole or higher of 1,1,1,3,3-pentafluoropropane as a main product and slight amounts (less than 1% by mole) of 3-chloro-1,1,1,3-tetrafluoropropane and 3,3-dichloro-1,1,1-trifluoropropane as byproducts.

After the operation for 120 hours under the above described conditions, the reaction was stopped and the test piece was recovered. This test was conducted on each material according to the above described procedure, and the corrosion rates of the test pieces were calculated as described above. Results are listed in Table 1. It is noted that: a sample of the reaction liquid was obtained after the reaction was stopped and subjected to titrimetry and atomic absorption spectrophotometry, and it was found from results of these analyses that the fluorination catalyst was maintained at the concentration which is substantially the same as that at the beginning of the reaction.

(Test 2)

The test piece having a size same as in Test 1 was attached likewise to the inside of an autoclave which was similar to one used in Test 1. 72 g (0.2 mol) of $TaCl_5$ as a fluorination catalyst and 400 ml (20 mol) of liquid-state hydrogen fluoride were introduced into the autoclave. At that time, the fluorination catalyst ($TaCl_5$ in this test) was present in the reactor at an amount of 1 mole with respect to 100 moles of hydrogen fluoride, and therefore at an amount of about 1 mole with respect to 100 moles in total of hydrogen fluoride and the fluorination catalyst. Then, while the reaction temperature being controlled at 80° C. and the reaction pressure being kept at 1.1 MPa (gauge pressure) as in Test 1, the reactor was supplied with liquid-state 1,1,1,2,3,3-hexachloropropene as a halogenated hydrocarbon reaction raw material at a rate of 69.0 g/h as well as liquid-state hydrogen fluoride with controlling the amount of liquid-phase hydrogen fluoride so as to keep the weight of the reactor and its content constant (in other words, so as to keep a level of a liquid phase constant), whereby liquid-phase fluorination reaction was carried out. The supplied rate of liquid-state hydrogen fluoride was 78.4 g/h on an average.

In such a manner just described above, a fraction which contained hydrogen-containing fluorinated hydrocarbons (equivalent to about 55.0 g/h) was obtained. The hydrogen-containing fluorinated hydrocarbons of the fraction contained 99% by mole or higher of 2,3-dichloro-1,1,1,3,3-pentafluoropropane as a main product and a slight amount (less than 1% by mole) of 2,3,3-trichloro-1,1,1,3-tetrafluoropropane as a byproduct.

After the operation for 120 hours under the above described conditions, the reaction was stopped and the test piece was recovered. This test was conducted on each material according to the above described procedure, and the corrosion rates of the test pieces were calculated as described above. Results are listed in Table 1. It is noted that: a sample of the reaction liquid was obtained after the reaction was stopped and subjected to titrimetry and atomic absorption spectrophotometry, and it was found from results of these analyses that the fluorination catalyst was maintained at the concentration which is substantially the same as that at the beginning of the reaction.

(Test 3)

The test piece having a size same as in Test 1 was attached likewise to the inside of an autoclave which was similar to one used in Test 1. 60 g (0.2 mol) of $SbCl_5$ as a fluorination catalyst and 400 ml (20 mol) of liquid-state hydrogen fluoride were introduced into the autoclave. At that time, the fluorination catalyst ($SbCl_5$ as an antimony pentahalide in this test) was present in the reactor at an amount of 1 mole with respect to 100 moles of hydrogen fluoride, and therefore at an amount of about 1 mole with respect to 100 moles in total of hydrogen fluoride and the fluorination catalyst (the antimony pentahalide). Then, while the reaction temperature being controlled at 100° C. and the reaction pressure being kept at 1.5 MPa (gauge pressure), the reactor was supplied with liquid-state tetrachloroethylene as a halogenated hydrocarbon reaction raw material at a rate of 46.0 g/h as well as liquid-state hydrogen fluoride with controlling the amount of liquid-phase hydrogen fluoride so as to keep the weight of the reactor and its content constant (in other words, so as to keep a level of a liquid phase constant), whereby liquid-phase fluorination reaction was carried out. The supplied rate of liquid-state hydrogen fluoride was 29.6 g/h on an average.

In such a manner just described above, a fraction which contained hydrogen-containing fluorinated hydrocarbons (equivalent to about 39.6 g/h) was obtained. The hydrogen-containing fluorinated hydrocarbons of the fraction contained 99% by mole or higher of 2,2-dichloro-1,1,1-trifluoroethane as a main product and a slight amount (less than 1% by mole) of 2,3-dichloro-1,1-difluoroethane as a byproduct.

After the operation for 120 hours under the above described conditions, the reaction was stopped and the test piece was recovered. This test was conducted on each material according to the above described procedure, and the corrosion rates of the test pieces were calculated as described above. Results are listed in Table 1. It is noted that: a sample of the reaction liquid was obtained after the reaction was stopped and subjected to titrimetry and atomic absorption spectrophotometry, and it was found from results of these analyses that the fluorination catalyst was maintained at the concentration which is substantially the same as that at the beginning of the reaction.

TABLE 1

| Material of Test Piece | Corrosion Rate (mm/year) of Test Piece on Each Test | | |
|---|---|---|---|
| | Test 1 | Test 2 | Test 3 |
| MAT 21 | 0.05 | 0.007 | 0.09 |
| Hastelloy C22 | 1.10 | 0.21 | 1.55 |
| Monel 400 | 13.41 | 1.27 | 18.60 |
| Inconel 600 | 9.83 | 1.01 | 14.11 |
| Hastelloy B2 | 1.55 | 0.31 | 2.35 |

Referring Table 1, the corrosion rate of MAT 21 (trade name) which is an alloy having a composition preferable for the present invention is very small compared with other conventional materials of Hastelloy, Monel, and Inconel. Therefore, it is proved conformably with the results of Examples 1 to 5 that MAT 21 is suited for the alloy material of 18 to 20% by weight of chromium, 18 to 20% by weight of molybdenum, 1.5 to 2.2% by weight of at least one element selected from niobium and tantalum and the balance of nickel.

(Heat Treatment Test)

In this heat treatment test, immersion tests were conducted as to test pieces which had been subjected to heat treatment under various conditions as well as a test piece without heating, and the influence of the heat treatment upon the corrosion rate was verified. Test pieces each of which was made of MAT 21 were used in this test. The same conditions except for a heating condition were applied, and the test pieces were heated such that the whole of each test piece (the surface and the inside thereof) was heated.

At first, the test pieces made of MAT 21 and having a size same as in Test 1 described above had been subjected to heat treatment under heating conditions shown in following Table 2 (including no heating) respectively. The test piece was attached likewise to the inside of an autoclave which was similar to one used in Test 1. 60 g (0.2 mol) of $SbCl_5$ as a fluorination catalyst and 400 ml (20 mol) of liquid-state hydrogen fluoride were introduced into the autoclave. At that time, the fluorination catalyst ($SbCl_5$ as an antimony pentahalide in this test) was present in the reactor at an amount of 1 mole with respect to 100 moles of hydrogen fluoride, and therefore at an amount of about 1 mole with respect to 100 moles in total of hydrogen fluoride and the fluorination catalyst (the antimony pentahalide). Then, while the reaction temperature being controlled at 100° C. and the reaction pressure being kept at 1.5 MPa (gauge pressure), the reactor was supplied with liquid-state tetrachloroethylene as a halogenated hydrocarbon reaction raw material at a rate of 46.0 g/h as well as liquid-state hydrogen fluoride with controlling the amount of liquid-phase hydrogen fluoride so as to keep the weight of the reactor and its content constant (in other words, so as to keep a level of a liquid phase constant), whereby liquid-phase fluorination reaction was carried out. The supplied rate of liquid-state hydrogen fluoride was 29.6 g/h on an average.

In such a manner just described above, a fraction which contained hydrogen-containing fluorinated hydrocarbons (equivalent to about 39.6 g/h) was obtained. The hydrogen-containing fluorinated hydrocarbons of the fraction contained 99% by mole or higher of 2,2-dichloro-1,1,1-trifluoroethane as a main product and a slight amount (less than 1% by mole) of 2,3-dichloro-1,1-difluoroethane as a byproduct.

After the operation for 120 hours under the above described conditions, the reaction was stopped and the test piece was recovered. This test was conducted on each test piece according to the above described procedure, and the corrosion rates of the test pieces were calculated as described above. Results are listed in Table 2. It is noted that: a sample of the reaction liquid was obtained after the reaction was stopped and subjected to titrimetry and atomic absorption spectrophotometry, and it was found from results of these analyses that the fluorination catalyst was maintained at the concentration which is substantially the same as that at the beginning of the reaction.

TABLE 2

Corrosion Rate of Test Piece for Heat Treatment Condition

| Heat Treatment Condition | | |
|---|---|---|
| Heating Temperature (° C.) | Heating Period (hour) | Corrosion Rate (mm/year) |
| Non | Non | 0.09 |
| 500 | 1 | 0.08 |
| 500 | 3 | 0.05 |
| 600 | 1 | 0.09 |
| 600 | 3 | 0.08 |
| 800 | 1 | 0.09 |

As to MAT 21 (trade name) which is an alloy having a composition preferable for conducting the present invention, referring Table 2, the corrosion rates of the test pieces having subjected to the heat treatments were not greater than that of the test piece without heat treatment. The corrosion rates of the test pieces which were heated under respective conditions of 500° C. for 1 hour, 500° C. for 3 hours, and 600° C. for 3 hours were smaller than that of the test piece without heat treatment. Therefore, it is proved that the corrosion resistance of the alloy material can be enhanced also by subjecting the surface of the alloy material as described above (MAT 21 in this test) to the heat treatment.

What is claimed is:

1. A process for producing a hydrogen-containing fluorinated hydrocarbon in which at least one halogenated hydrocarbon reaction raw material which is selected from the group consisting of a chlorinated alkene and a hydrogen-containing chlorinated alkane is subjected to a fluorination reaction with a hydrogen fluoride reaction raw material in a liquid phase in a reactor in the presence of a fluorination catalyst so as to obtain a reaction mixture which comprises the hydrogen-containing fluorinated hydrocarbon as a reaction product, which process comprises using the reactor having a reactor portion which is able to contact with the reaction mixture, at least a part of the reactor portion being made of an alloy material of 18 to 20% by weight of chromium, 18 to 20% by weight of molybdenum, 1.5 to 2.2% by weight of at least one element selected from niobium and tantalum and the balance of nickel.

2. The process according to claim 1 which comprises using the reactor wherein substantially the whole of the reactor portion which is able to contact with the reaction mixture is made of said alloy material.

3. The process according to claim 1, wherein said alloy material has been processed so as to cause a residual stress in its surface portion.

4. The process according to claim 1, wherein said alloy material has been subjected to a heat treatment.

5. The process according to claim 1, wherein the alloy material further contains not more than 1% by weight of cobalt.

6. The process according to claim 1, wherein the alloy material further contains not more than 1% by weight of iron.

7. The process according to claim 1, wherein the fluorination catalyst comprises at least one compound selected from the group consisting of an antimony pentahalide, a niobium pentahalide and a tantalum pentahalide, and an antimony trihalide, a niobium trihalide and a tantalum trihalide.

8. The process according to claim 1, wherein the fluorination reaction is conducted in the presence of a reaction solvent, and hydrogen fluoride functions not only as the reaction raw material but also as the solvent.

9. The process according to claim 7, wherein the antimony pentahalide is used as the fluorination catalyst and present in the reactor in a ratio of not larger than 3 moles or not smaller than 30 moles with respect to 100 moles in total of hydrogen fluoride and the antimony pentahalide which are present in the reactor.

10. The process according to claim 1, wherein the halogenated hydrocarbon reaction raw material is a chlorinated ethylene which is expressed by the following general formula (1):

$$C_2H_aF_bCl_c \qquad (1)$$

wherein a, b, and c are integers satisfying: a+b+c=4; a≧0; b≧0; and c≧1.

11. The process according to claim 1, wherein the halogenated hydrocarbon reaction raw material is a hydrogen-containing chlorinated methane which is expressed by the following general formula (2):

$$CH_dF_eCl_f \qquad (2)$$

wherein d, e, and f are integers satisfying: d+e+f=4; d≧1; e≧0; and f≧1.

12. The process according to claim 1, wherein the halogenated hydrocarbon reaction raw material is a hydrogen-containing chlorinated ethane which is expressed by the following general formula (3):

$$C_2H_gF_hCl_i \qquad (3)$$

wherein g, h, and i are integers satisfying: g+h+i=6; g≧1; h≧0; and i≧1.

13. The process according to claim 1, wherein the halogenated hydrocarbon reaction raw material is a hydrogen-containing chlorinated propane which is expressed by the following general formula (4):

$$C_3H_jF_kCl_l \qquad (4)$$

wherein j, k, and l are integers satisfying: $j+k+l=8$; $j \geq 1$; $k \geq 0$; and $l \geq 1$.

14. The process according to claim 1, wherein the halogenated hydrocarbon reaction raw material is a chlorinated propene which is expressed by the following general formula (5):

$$C_3H_mF_nCl_o \qquad (5)$$

wherein m, n, and o are integers satisfying: $m+n+o=6$; $m \geq 0$; $n \geq 0$; and $o \geq 1$.

15. The process according to claim 1, wherein the halogenated hydrocarbon reaction raw material is a chlorinated butadiene which is expressed by the following general formula (6):

$$C_4H_pF_qCl_r \qquad (6)$$

wherein p, q, and r are integers satisfying: $p+q+r=6$; $p \geq 0$; $q \geq 0$; and $r \geq 1$.

16. The process according to claim 10, wherein the halogenated hydrocarbon reaction raw material is tetrachloroethylene and the hydrogen-containing fluorinated hydrocarbon which is produced through the reaction is 2,2-dichloro-1,1,1-trifluoroethane.

17. The process according to claim 10, wherein the halogenated hydrocarbon reaction raw material is trichloroethylene and the hydrogen-containing fluorinated hydrocarbon which is produced through the reaction is 2-chloro-1,1,1-trifluoroethane.

18. The process according to claim 11, wherein the halogenated hydrocarbon reaction raw material is dichloromethane and the hydrogen-containing fluorinated hydrocarbon which is produced through the reaction is difluoromethane.

19. The process according to claim 13, wherein the halogenated hydrocarbon reaction raw material is at least one substituted propane selected from the group consisting of 1,1,1,3,3-pentachloropropane and a partially fluorinated compound thereof and the hydrogen-containing fluorinated hydrocarbon which is produced through the reaction is 1,1,1,3,3-pentafluoropropane.

20. The process according to claim 14, wherein the halogenated hydrocarbon reaction raw material is 1,3,3,3-tetrachloropropene and the hydrogen-containing fluorinated hydrocarbon which is produced through the reaction is 1,1,1,3,3-pentafluoropropane.

21. The process according to claim 14, wherein the halogenated hydrocarbon reaction raw material is 1-chloro-3,3,3-trifluoropropene and the hydrogen-containing fluorinated hydrocarbon which is produced through the reaction is 1,1,1,3,3-pentafluoropropane.

22. The process according to claim 14, wherein the halogenated hydrocarbon reaction raw material is at least one substituted propene selected from the group consisting of 1,1,1,2,3,3-hexachloropropene and a partially fluorinated compound thereof and the hydrogen-containing fluorinated hydrocarbon which is produced through the reaction is 2,3-dichloro-1,1,1,3,3-pentafluoropropane.

23. The process according to claim 15, wherein the halogenated hydrocarbon reaction raw material is 1,1,2,3,4,4-hexachlorobutadiene and the hydrogen-containing fluorinated hydrocarbon which is produced through the reaction is 2-chloro-1,1,1,4,4,4-hexafluorobutene.

* * * * *